United States Patent [19]

Komura

[11] Patent Number: 4,544,121

[45] Date of Patent: Oct. 1, 1985

[54] SUPPORT APPARATUS FOR MEDICAL APPLIANCE

[75] Inventor: Seiichi Komura, Sumiyoshi, Japan

[73] Assignee: Tokyo Kogaku Kikai Kabushiki Kaisha, Tokyo, Japan

[21] Appl. No.: 688,284

[22] Filed: Jan. 4, 1985

Related U.S. Application Data

[63] Continuation of Ser. No. 462,094, Jan. 28, 1983, abandoned.

[30] Foreign Application Priority Data

Feb. 3, 1982 [JP] Japan .............. 57-12977[U]

[51] Int. Cl.$^4$ ............................ F16M 13/00
[52] U.S. Cl. .................. 248/331; 248/542; 192/129 R
[58] Field of Search ........... 248/331, 544, 648, 297.1, 248/325, 162.1; 192/129 R; 16/1 C; 187/81, 82, 89

[56] References Cited

U.S. PATENT DOCUMENTS

| 602,517 | 4/1898 | McFadden | 248/163 |
|---|---|---|---|
| 1,023,711 | 4/1912 | Balazs | 187/82 |
| 1,066,399 | 7/1913 | Garrecht | 248/325 |
| 2,974,920 | 3/1961 | Spaulding | 248/542 |
| 4,360,180 | 11/1982 | Bruneau | 248/162.1 |

FOREIGN PATENT DOCUMENTS

| 385001 | 3/1963 | Japan . |
|---|---|---|
| 45-31550 | 12/1970 | Japan . |
| 49-5253 | 2/1974 | Japan . |
| 51-101776 | 8/1976 | Japan . |

Primary Examiner—J. Franklin Foss
Assistant Examiner—Robert A. Olson
Attorney, Agent, or Firm—Brumbaugh, Graves, Donohue & Raymond

[57] ABSTRACT

A support apparatus for a medical appliance includes a support, a lifter for mounting the medical appliance, a counterweight, a wire with one end connected to the lifter and the other end connected to the counterweight, the wire being passed over a first pulley mounted rotatably on the support, whereby the medical appliance can be moved vertically with weights of the lifter and the counterweight being substantially balanced with each other.

The lifter includes a braking device mounted thereon through parallel link arms extending obliquely downward, a stopper device adapted for engagement with the braking device, a rotatable second pulley, and a spring with one end connected to one end of the braking, the one end of the wire is passed over the second pulley and then connected to the other end of the braking device whereby the braking device is normally held away from a side surface of the support and made to abut against the stopper under the weight of the counterweight acting against influence of the spring, but the braking device is brought into contact with the side surface of the support under the tensile force of the spring when tension of the wire decreases.

12 Claims, 2 Drawing Figures

SUPPORT APPARATUS FOR MEDICAL APPLIANCE

This application is a continuation of application Ser. No. 462,094, filed on Jan. 28, 1983, now abandoned.

BACKGROUND OF THE INVENTION

1. Field of the Invention

The present invention relates primarily to a ceiling-suspended support apparatus for medical appliances supported so as to be movable vertically, such as an operation microscope, X-ray equipment, laser scalpel or the like, and more particularly to an improvement in the fall-prevention mechanism thereof.

2. Description of the Prior Art

Well known ceiling-suspended support apparatuses for medical appliances are arranged such that a pulley is rotatably supported above a lifter adapted to hold a medical appliance at the lower end thereof, and move vertically in a support casing, and the lifter and a counterweight are held at opposite ends of a wire passed over the pulley so as to balance the weight of each other. Various types of fall-prevention mechanism have been proposed for preventing the fall of the lifter when the tension in the wire of this type of support apparatus is reduced by the wire breaking or coming off the pulley. For example, Japanese Utility Model Publication No. 5253/1974 disclosed a fall-prevention mechanism for the support apparatus. The mechanism is arranged such that a wedge which is pulled toward a lifter by means of a spring is normally pulled by a wire connected to a counterweight in the direction opposite to the direction of pull of the spring against the force thereof, so that when the wire breaks, the wedge is pulled by means of the tensile force of the spring so as to press against a slide pin, which brings a braking member into pressure-contact with a support wall, thereby preventing the fall of the lifter by means of the frictional force of the braking member.

In such a conventional supporting apparatus for a medical appliance, however, the slide pin pressing the fall-prevention braking member against the support wall has a fixed direction of movement which is perpendicular to the axial direction of the support, and also the direction of the compression force of the braking member is perpendicular to the axial direction of the support. Therefore, a much larger compression force is required in order to prevent the lifter falling. Since the spring means pulling the wedge must also have a large tension in proportion to the compression force, it is also necessary to increase the size of the counterweight to balance its weight with that of the lifter against the force of the spring means, resulting in an undesirable increase in the size of the support itself, solely to suspend the counterweight. Moreover, in order to increase the frictional force of the braking means, it is necessay to increase the contact area thereof, and this brings about an increase in the size in the fall-prevention mechanism itself, and the support apparatus is larger in size as a whole, resulting in a higher cost. In addition, a wider installation area is required, so that the operating room, etc., where such a support apparatus is installed is more cramped, which could be inconvenient to the surgeon or other operator of the support apparatus.

Moreover, since a conventional support apparatus for a medical appliance has no means for preventing the counterweight falling, a fall of the counterweight may destroy the electrical circuits, etc., inside the stand.

SUMMARY OF THE INVENTION

It is, therefore, a first object of the invention to provide a novel support apparatus for a medical appliance which is capable of preventing the fall of the lifter when the tension of the wire decreases because the wire has broken, or it has come off the pulley, or because of other accidents, thereby overcoming the above problems of the prior art.

It is a second object of the invention to provide a support apparatus for a medical appliance having a simplified braking means preventing the fall of the lifter, and which is capable of braking reliably even if the actuating member for the braking uses a small force.

It is a third object of the invention to provide a novel support apparatus for a medical appliance which is also capable of preventing the fall of the counterweight when the tension of the wire decreases because the wire has broken, or it has come off the pulley, or because of other accidents.

It is a fourth object of the invention to provide a ceiling-suspended support apparatus for a medical appliance which is capable of fulfilling the above three objects.

According to the invention, the above and other objects can be accomplished by a support apparatus for a medical appliance comprising support means; lifter means for mounting said medical appliance; counterweight means; and wire means with one end connected to the lifter means and the other end connected to the counterweight means, the wire means being passed over first pulley means rotatably mounted on the support means, whereby the medical appliance can be moved vertically with the weights of the lifter means and the counterweight means substantially balanced with each other, characterized in that the lifter means includes: braking means mounted thereon through parallel link arms extended obliquely downward; stopper means adapted for engagement with the braking means; second rotatable pulley means; spring means with one end thereof connected to one end of the braking means, one end of the wire means being passed over the second pulley means and is connected to the other end of the braking means, so that the braking means is normally held away from the side surfaces of the support means and is made to abut against the stopper means by the weight of the counterweight means acting against the force of the spring means, but the braking means is brought into contact with the side surface of the support by the force of the spring means when the tension of the wire decreases.

According to the invention having the above arrangement, when the tension of the wire decreases, it is only necessary to make the spring means bring the braking means into contact with the side surface of the support, and thereafter the lifter's own weight is converted into a compression force of the braking means against the support through the parallel link arms. Therefore, it is unnecessary for the spring means to have a very large tensile force, and also the braking means can be made more compact than that of a conventional supporting apparatus. Moreover, since the tensile force of the spring means is small, it is possible to reduce the weight of the counterweight, which is the sum of the weights of the lifter, etc., and the force opposing the tensile force of the spring means. Accordingly, the support apparatus itself, which contains the lifter and counterweight, can be made more compact and lightweight.

DETAILED DESCRIPTION OF THE PREFERRED EMBODIMENT

Figure 1:
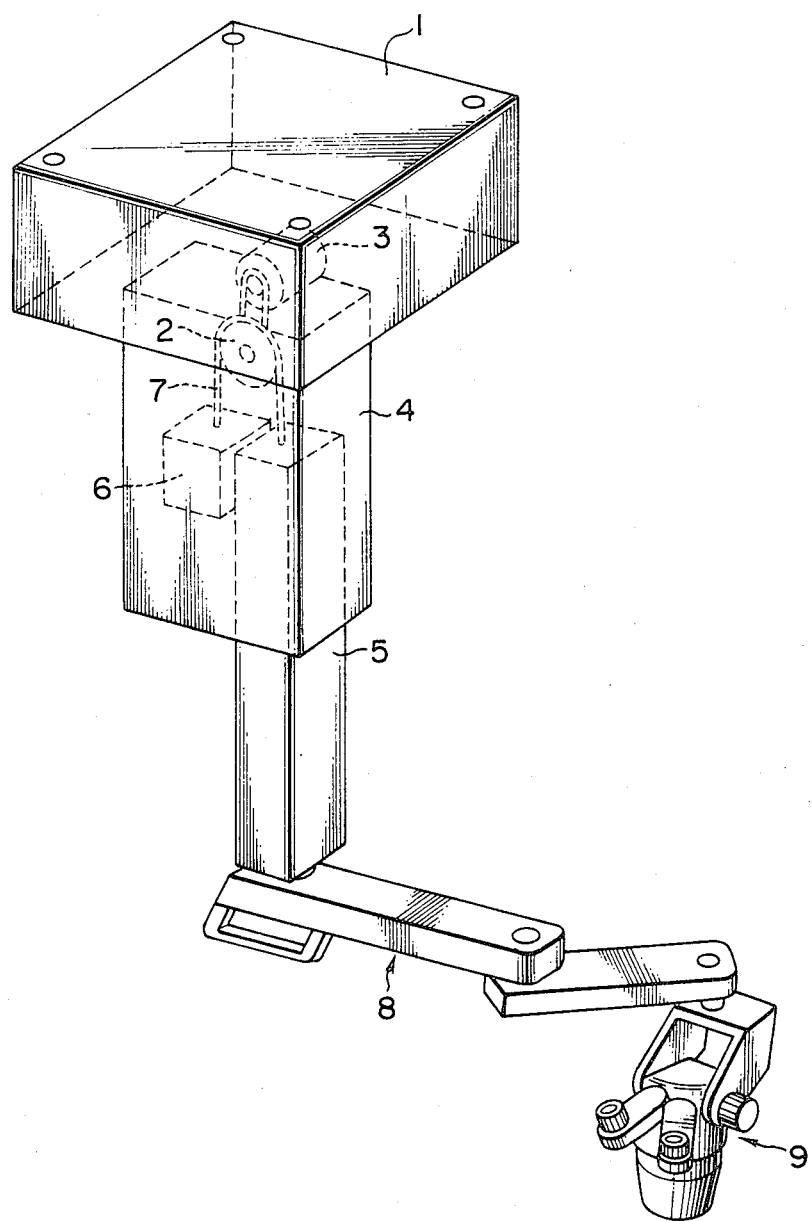
FIG. 1 is a perspective view of a support apparatus for a medical appliance in accordance with one preferred embodiment of the invention.

FIG. 1 is a perspective view of a support apparatus for a medical appliances (referred to simply as "support apparatus" hereinafter) according to the invention. A base part 1 houses an electrical unit, not shown, and a motor 3 for rotating a first pulley or sprocket wheel 2 (referred to simply as "pulley" hereinafter) by a belt or the like, and is fixed to the ceiling of an operating theater, examination room or the like. A support 4 in the shape of a hollow rectangular parallelepiped is suspended from the lower part of the base part 1. Inside the support 4, a lifter 5 in the shape of a hollow rectangular parallelepiped having an arm 8 mounted on the lower end thereof, and a counterweight 6, are suspended by a wire or chain 7 (referred to simply as "wire" hereinafter) passed over the first pulley 2, the counterweight and lifter being connected to each end of the wire 7 and balanced with each other. An operation microscope 9 or the like is mounted on the end of the arm 8.

Figure 2:
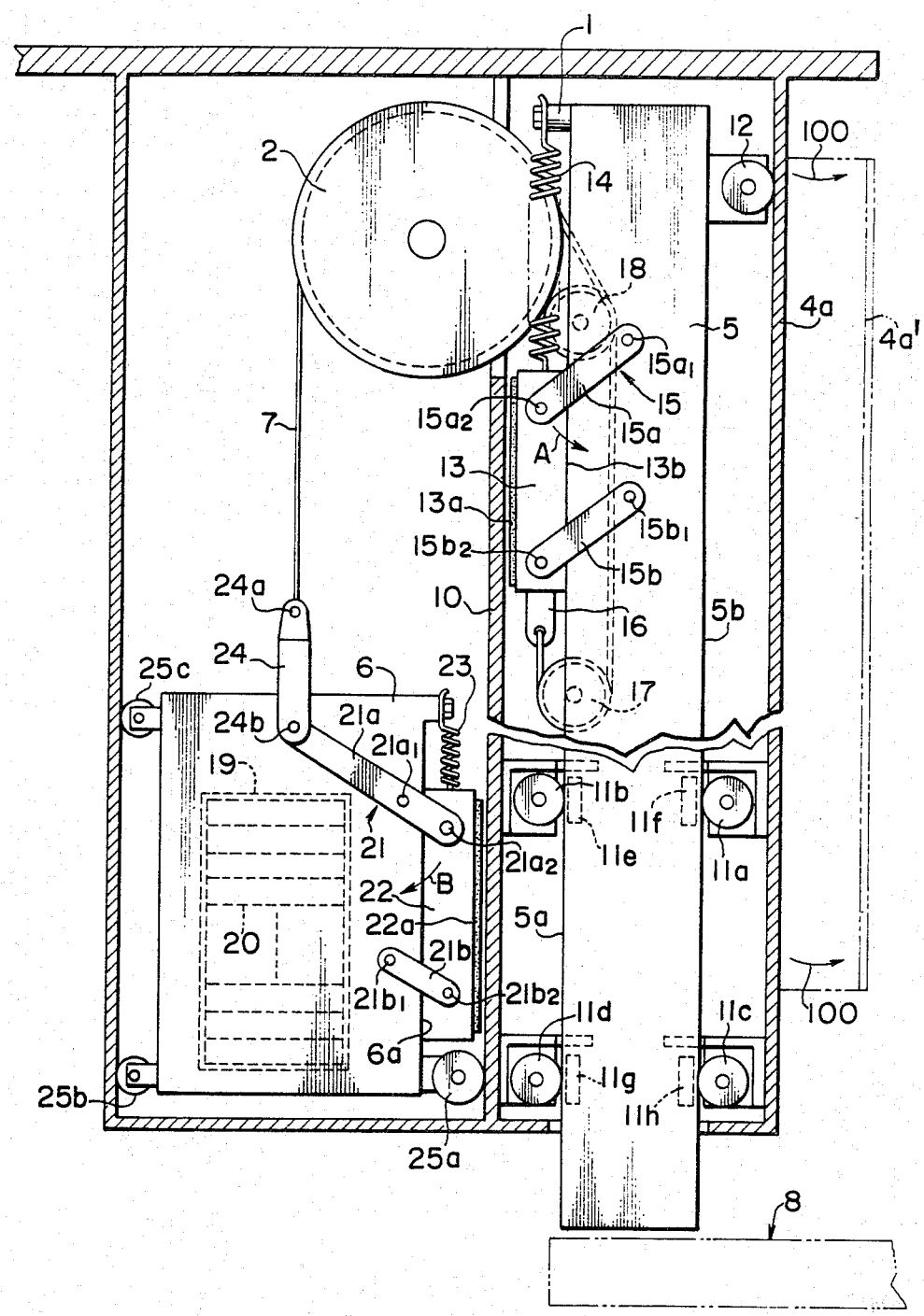
FIG. 2 is a sectional elevational view of the support part of the support apparatus for medical appliances shown in FIG. 1.

FIG. 2 is a sectioned elevational view of the support 4 of FIG. 1, illustrating the mechanism preventing the fall of the lifter 5 and the counterweight 6 of the support apparatus according to the invention. The inside of the support 4 is partitioned into two chambers by an intermediate wall 10. One of the chambers houses the lifter 5, while the other houses the counterweight 6. The lifter 5 is clamped at points on its outer surface and guide so as to be slidable vertically by means of guide wheels 11a, 11b, . . . 11h, each mounted on one of the four inner walls of the support 4, and four guide wheels, not shown, each facing one of the guide wheels 11e, 11f, 11g, 11h. A guide wheel 12 adapted to roll along the inner wall surface of the support 4 is mounted on a side of the lifter 5 near the upper end thereof facing an inner wall of the support 4.

The ends $15a_1$ and $15b_1$ of link arms 15a, 15b, respectively, of a parallel link mechanism 15 are pivotably mounted on a side surface 5b of the lifter 5. A pivotable brake pad 13 is mounted on the other ends $15a_2$, $15b_2$ of the link arms 15a, 15b extended obliquely downward substantially parallel to the side surface 5a of the lifter 5. A rubber brake shoe 13a is attached to the brake pad 13 so as to be used when the brake pad 13 is brought into contact with the intermediate wall 10 of the support 4. The brake pad 13 has one end thereof fixed to one end of a spring 14 whose other end is secured to the upper end of the lifter 5, so as to be pulled upward at all times. In addition, the wire 7 which pulls the brake pad 13 downward against the force of the spring 14 is connected to a hanger boss 16 at the lower end of the brake pad 13 so that the parallel link mechanism pivots in the direction of the arrow A, so that the brake shoe 13a is pulled away from the intermediate wall 10, and the brake pad surface 13b is brought into contact with the side surface 5a of the lifter 5. The wire 7 is directed upward by means of a second pulley 17 supported rotatably by the lifter 5, and is passed over the first pulley 2 via a third pulley 18 which is supported rotatably by the lifter 5 above the second pulley 17, and is then connected to the counterweight 6. The counterweight 6 is formed in the shape of a case having a housing 19 provided therein. The housing 19 houses a plurality of single weights 20 equivalent to the total weight of the medical appliance suspended by the lifter 5 and that of the lifter 5 itself. A brake pad 22 is mounted through a parallel link mechanism 21, in the same way as described above, while in contact with a surface 6a of the counterweight 6 on the side of the intermediate wall 10. Mounting ends $21a_1$, $21b_1$ of the link arms 21a, 21b, respectively, of the parallel link mechanism 21 are pivotably mounted on a side surface of the counterweight 6, while the other mounting ends $21a_2$, $21b_2$ are pivotally mounted on the brake pad 22. It is to be noted that one end of the link arm 21a extends further from the mounting end $21a_1$ mounted pivotally on the counterweight 6, and is connected pivotably to one end 24b of a hanger arm 24. The other end 24a of the hanger arm 24 is connected to the end of the wire 7 passed over the first pulley 2 and then extending downward, so as to be pulled upward at all times. Therefore, the parallel link mechanism 21 is pivoted in the direction of the arrow B about the mounting end $21a_1$ of the link arm 21a, so that the brake pad 22 is held away from the intermediate wall 10 and the link arms 21a, 21b are placed obliquely downward parallel to each other. In addition, a spring 23 imparting a constant upward force is secured to the upper end of the brake pad 22, and the other end of the spring 23 is fixed to the upper end of the counterweight 6. A rubber brake shoe 22a is attached to the surface of the brake pad 22 which is brought into contact with the intermediate wall 10. The counterweight 6 is provided with guide wheels 25a, 25b, 25c which run along the side walls inside the case of the support 4 while in contact with it.

The operation of the support apparatus for a medical appliance will be described hereinunder.

When the lifter 5 is lowered and the arm 8 is extended to direct the operation microscope 9 toward the affected part of a patient in such a way that the lifter 5 is moved vertically by the rotation of the first pulley 2 moved by means of the motor 3 or the like, the counterweight 6 is pulled upward by the wire 7, while maintaining the balance. Because of this balance, the brake pad 13 on the side of the lifter 5 is pulled downward against the tension of the spring 14 by the tension of the wire 7 pulled by the weight of the counterweight 6. Consequently, the link arms 15a, 15b of the parallel link mechanism 15 on which the brake pad 13 is mounted receive a force which causes the parallel link mechanism 15 to rotate counterclockwise as shown by the arrow A. As a result, the rear surface 13b of the brake pad 13 is brought into contact with the side surface of the lifter 5, while the brake shoe 13a of the brake pad 13 is held away from the intermediate wall 10. The brake pad 22 on the side of the counterweight 6 is similarly pulled in the direction of the arrow B against the tension of the spring 23 by the action of the parallel link mechanism 21, since the hanger arm 24 is pulled upward by the tension of the wire 7, so that the brake shoe 22a is held away from the intermediate wall 10. As described above, when the first pulley 2 is rotated by the motor 3, the lifter 5 and the counterweight 6 are moved vertically as required, since they are suspended inside the support 4, balancing each other.

Next, the operation of the fall-prevention mechanism in an emergency such as when the wire breaks or comes off the pulley will be described. In such a case, since the tension of the wire 7 is released, the brake pads 13 and 22 are pulled upward by the tensions in the springs 14 and 23, respectively. Consequently, the parallel link mechanisms 15 and 21 are instantaneously rotated in the directions opposite to the directions of the arrows A, B, respectively, pressing the brake pads 13 and 22 against the intermediate wall 10. This makes the brake shoes 13a, 22a attached to the brake pads 13, 22, respectively, rub against the intermediate wall 10, thereby preventing the lifter 5 and the counterweight 6 from falling by means of the frictional forces thereof. In addition, since the lifter 5 and the counterweight 6 attempt to fall, their own weights further increase the rotational forces of the parallel link mechanisms 15, 21, respectively, so that the brake shoes 13a, 22a are pressed against the intermediate wall 10 with larger forces, thereby allowing the frictional forces to increase and hence the braking actions to be intensified. It is to be noted that the parallel link mechanisms 15,21 are arranged so as to be inclined constantly downward even when braking, and are mounted so that they are prevented from becoming horizontal. It is to be noted also that although the brake pad 13 is adapted to be brought into contact with the intermediate wall 10 in the above embodiment, the arrangement is not exclusive and an arrangement may be employed in which the brake pad 13 is brought into contact with the inner surface of an outer wall 4a of the support 4. In such a case, it will be convenient for the maintenance of the fall-prevention mechanism, if part of the outer wall 4a is formed into a door which can be opened in the direction of the arrow 100, as shown by the dot-dot-dashed lines in the figure.

When the wire breaks or a similar accident happens, the brake pads attached to the parallel link mechanisms are instantaneously pulled upward by the tensile forces of the respective coiled springs. Consequently, as the link arms pivot toward the intermediate wall of the support, the brake pads are brought into strong contact therewith, producing strong braking forces, thereby preventing the fall of the lifter and the counterweight. Accordingly, each brake pad can be brought into contact with the intermediate wall by using only sufficient force to raise the brake pad, and the frictional force thereof and the weight of the lifter or counterweight attempting to fall presses the brake pad against the intermediate wall more strongly through the corresponding link arms. Therefore the frictional force produced by the surface of the corresponding brake shoe is increased, thereby allowing a large braking force to be obtained. Since the fall-prevention mechanism has such an arrangement, each coiled spring need have only a small tensile force, and the mechanism itself can be made compact, and yet a reliable fall prevention can be effected. Moreover, since the fall-prevention mechanism for the counterweight is mounted on the support apparatus for the medical appliance, it is possible to provide a safe support apparatus eliminating the possibility that the fall of the counterweight due to such an accident as the breaking of the wire could damage other appliances. Furthermore, since the brake pads are connected to respective parallel link mechanisms, satisfactory braking forces can be obtained by selecting appropriate frictional areas according to the weights of the lifter and the counterweight, so that a safer support apparatus can be designed. Although the invention has been described for a suspended support apparatus with reference to the illustrated example of a fall-prevention mechanism, the suspended support apparatus is not exclusive and the fall-prevention mechanism according to this invention can, of course, be widely employed for balance types of support apparatus in various fields.

What is claimed is:

1. A support apparatus for a medical appliance comprising support means having a vertical side surface and vertical guide means, lifter means adapted for mounting said medical appliance and positioned in said support means to be guided in vertical direction by said guide means, said lifter means having a vertical side surface adjacent to said vertical side surface of the support means, counterweight means, first pulley means provided on said support means at a level higher than said counterweight means for rotation about a horizontal axis, parallel link means including a plurality of parallel link arms each having one end pivotably connected with said lifter means and extending obliquely downward towards said vertical side surfaces of said support means, brake shoe means mounted on the other end of said parallel link arms and located between said vertical side surface of said lifter means and said vertical side surface of said support means, said brake shoe means having a friction surface facing the vertical side surface of said support means, a relatively small force spring means for biasing said brake shoe means upwardly with respect to said lifter means, second pulley means provided on said lifter means at a level below said brake shoe means for rotation about a horizontal axis, wire means having one end connected to said counterweight means and passing around and extending downwardly from said first pulley means and passing around said second pulley means and having its other end connected to the brake shoe means, such that normal tension in said wire means forces said brake shoe means in the downward direction against the biasing force of said spring means and causes the parallel link arms to be held downward so that the brake shoe means is maintained away from the vertical side surface of the support means and in abutting engagement with said vertical side surface of said lifter means, and such that decreased tension in said wire means permits the friction surface of the brake shoe means to be forced into contact with the vertical side surface of the support means under the biasing force of the relatively small force spring means, at which time said parallel link means allows the brake shoe means to be forced more tightly against the vertical side surface of the support means by the weight of the lifter means.

2. A support apparatus for a medical appliance in accordance with claim 1 in which said support means includes second vertical guide means for guiding said counterweight means and a second vertical side surface adjacent to said counterweight means, said counterweight means having a second vertical side surface adjacent to said second vertical side surface of the support means, and further comprising a second parallel link means including a plurality of second parallel link arms pivotably mounted on said counterweight means, said second parallel link arms extending from said counterweight means obliquely downward toward said second vertical side surface of said support means, second brake shoe means mounted on free ends of said second parallel link arms and having a friction surface facing the second vertical surface of the support means, second relatively small force spring means biasing said second brake shoe means upwardly with respect to said counterweight means, said wire means being connected at one end to said counterweight means through said second parallel link means such that normal tension in said wire means causes the second parallel link arms to be held downward against the biasing force of the second spring means so as to maintain the second brake shoe means away from said second vertical side surface of the support means and in abutting engagement with the second vertical side surface of the counterweight means, and such that decreased tension in said wire means permits the friction surface of the second brake shoe means to be forced into contact with the second vertical side surface of the support means under the biasing force of the second relatively small force spring means, at which time, said second parallel link means allows the second brake means to be forced more tightly against the second vertical side surface of the support means by the weight of the counterweight means.

3. A support apparatus for a medical appliance according to claim 1, in which said first pulley means is a drive pulley connected to motor means for pulling said wire means to move said lifter means vertically.

4. A support apparatus for a medical appliance according to claim 2, in which said support means is suspended from a ceiling and has a hollow structure having a first chamber and a second chamber separated by a vertical intermediate wall, said lifter means being arranged so as to be moved vertically within said first chamber, said counterweight being arranged so as to be moved vertically within said second chamber, said first and second vertical side surfaces being provided by said vertical intermediate wall.

5. A support apparatus for a medical appliance according to claim 4, in which said friction surface of each said brake shoe means is a planar contact surface.

6. A support apparatus for a medical appliance according to claim 5, in which each said brake includes a rubber brake shoe having a friction surface.

7. A support apparatus for a medical appliance according to claim 4, in which said counterweight means includes a housing provided with a hollow of rectangular cross-section open on at least one side for receiving weights, and a plurality of weight of rectangular cross-section disposed within said hollow.

8. A support apparatus for a medical appliance according to claim 2, in which said support means has a hollow structure suspended from a ceiling, said lifter means and said counterweight means being arranged within said hollow structure, said first vertical side surface of the support means being provided by an inner side wall of said support means.

9. A support apparatus for a medical appliance according to claim 8, in which said inner side wall of said support means defining said first vertical side surface of said support means is in the form of a door which can be opened from outside said support means.

10. A support apparatus for a medical appliance according to claim 8, in which said friction surface of each said brake shoe means is a planar contact surface.

11. A support apparatus for a medical appliance according to claim 10, in which each said brake shoe means includes a rubber brake shoe providing said planar contact surface.

12. A support apparatus for a medical appliance according to claim 8, in which said counterweight means includes a housing provided with a hollow of rectangular cross-section open on at least one side for receiving weights, and a plurality of weights of rectangular cross-section disposed within said hollow.

* * * * *